United States Patent
Krachon et al.

(10) Patent No.: US 10,328,278 B2
(45) Date of Patent: Jun. 25, 2019

(54) DEVICE FOR LOADING BRACHYTHERAPY SEEDS INTO IMPLANTATION SLEEVES

(71) Applicant: IsoRay Medical, Inc., Richland, WA (US)

(72) Inventors: Michael L. Krachon, Atlanta, GA (US); Patrick Strane, Atlanta, GA (US); Michael A Fisher, Lawrenceville, GA (US); Keooudone Thavone, Connell, WA (US)

(73) Assignee: Isoray Medical, Inc, Richland, WA (US)

( * ) Notice: Subject to any disclaimer, the term of this patent is extended or adjusted under 35 U.S.C. 154(b) by 0 days.

(21) Appl. No.: 16/165,178

(22) Filed: Oct. 19, 2018

(65) Prior Publication Data

US 2019/0126065 A1    May 2, 2019

Related U.S. Application Data

(60) Provisional application No. 62/580,837, filed on Nov. 2, 2017.

(51) Int. Cl.
*A61N 5/00* (2006.01)
*A61N 5/10* (2006.01)

(52) U.S. Cl.
CPC ...... *A61N 5/1007* (2013.01); *A61N 2005/101* (2013.01); *A61N 2005/1009* (2013.01); *A61N 2005/1024* (2013.01)

(58) Field of Classification Search
CPC .......... A61N 5/1007; A61N 2005/1008; A61N 2005/1009; A61N 2005/101
USPC ........................................................ 600/1–8
See application file for complete search history.

(56) References Cited

U.S. PATENT DOCUMENTS

| | | |
|---|---|---|
| 2,153,889 A | 4/1939 | Hames et al. |
| 3,351,049 A | 11/1967 | Lawrence |
| 3,670,729 A | 6/1972 | Bennett et al. |
| 4,402,308 A | 9/1983 | Scott |
| 4,447,223 A | 5/1984 | Kaye et al. |
| 4,451,254 A | 5/1984 | Dinius et al. |
| 4,697,575 A | 10/1987 | Horowitz |
| 4,754,745 A | 7/1988 | Horowitz |
| 4,759,345 A | 7/1988 | Mistry |
| 4,815,449 A | 3/1989 | Horowitz |
| 5,147,295 A | 9/1992 | Stewart |

(Continued)

OTHER PUBLICATIONS

International Search Report and Written Opinion for PCT/US18/56677 dated Mar. 6, 2019.

*Primary Examiner* — John P Lacyk
(74) *Attorney, Agent, or Firm* — Etherton Law Group, LLC

(57) ABSTRACT

A device for loading brachytherapy seeds and spacers into a sleeve. The device holds two or more seed or spacer cartridges of different radioactive species and dosage. The user rotates a selector for selecting a desired cartridge and, with each depression of a spring-biased plunger, pushes a seed or spacer into a channel in an inspection area. The process is repeated for the desired number and order of seeds and spacers in sequence to form a strand. The strand can be seen in the channel with the unaided eye through a transparent window. The window is part of a hinged door that can be opened and the sequence of the seeds and spacers rearranged with forceps. Once the strand is arranged as desired, it is pushed into a sleeve in a removable sleeve holder. During radiation treatment, the filled sleeve is removed from the sleeve holder and implanted into patient.

20 Claims, 26 Drawing Sheets

(56) References Cited

U.S. PATENT DOCUMENTS

| | | |
|---|---|---|
| 5,242,373 A | 9/1993 | Scott |
| 5,460,592 A | 10/1995 | Langton et al. |
| 5,906,574 A | 5/1999 | Kan |
| 5,928,130 A | 7/1999 | Schmidt |
| 6,007,474 A | 12/1999 | Rydell |
| 6,010,446 A | 1/2000 | Grimm |
| 6,095,967 A | 8/2000 | Black et al. |
| 6,264,600 B1 | 7/2001 | Grimm |
| 6,267,718 B1 | 7/2001 | Vitali et al. |
| 6,270,472 B1 | 8/2001 | Antaki et al. |
| 6,358,195 B1 | 3/2002 | Green |
| 6,450,937 B1 | 9/2002 | Mercerau et al. |
| 6,514,193 B2 | 2/2003 | Kaplan |
| 6,537,192 B1 | 3/2003 | Elliott et al. |
| 6,551,275 B2 | 4/2003 | Kaplan |
| 6,554,760 B2 | 4/2003 | Lamoureaux et al. |
| 6,561,967 B2 | 5/2003 | Schmidt |
| 6,572,525 B1 | 6/2003 | Yoshizumi |
| 6,575,890 B2 | 6/2003 | Kaplan et al. |
| 6,599,232 B2 | 7/2003 | Kaplan |
| 6,616,593 B1 | 9/2003 | Elliott et al. |
| 6,616,594 B2 | 9/2003 | Kaplan |
| 6,626,817 B2 | 9/2003 | Luth |
| 6,638,206 B2 | 10/2003 | Green et al. |
| 6,656,107 B1 | 12/2003 | Pederson et al. |
| 6,669,622 B2 | 12/2003 | Reed et al. |
| 6,722,404 B2 | 4/2004 | Osborne |
| 6,723,037 B2 | 4/2004 | Hamazaki et al. |
| 6,746,661 B2 | 6/2004 | Kaplan |
| 6,761,680 B2 | 7/2004 | Terwilliger et al. |
| 6,846,283 B2 | 1/2005 | Green et al. |
| 7,001,326 B2 | 2/2006 | Reed |
| 7,041,048 B2 | 5/2006 | Drobnik |
| 7,361,135 B2 | 4/2008 | Drobnik |
| 7,588,528 B2 | 9/2009 | Drobnik |
| 7,666,161 B2 | 2/2010 | Nash |
| 7,731,683 B2 | 6/2010 | Jang et al. |
| 7,776,310 B2 | 8/2010 | Kaplan |
| 7,959,608 B2 | 6/2011 | Nash |
| 7,976,528 B2 | 7/2011 | Nash |
| 7,988,612 B2 | 8/2011 | Drobnik |
| 8,152,782 B2 | 4/2012 | Jang et al. |
| 8,360,951 B2 | 1/2013 | Schreiber et al. |
| 8,366,597 B2 | 2/2013 | Hentrich |
| 8,641,593 B2 | 2/2014 | Drobnik |
| 8,752,701 B2 | 6/2014 | Jacobs |
| 8,808,157 B2 | 8/2014 | Watson |
| 8,821,835 B2 | 9/2014 | Kaplan |
| 8,920,402 B2 | 12/2014 | Nash |
| 9,050,458 B2 | 6/2015 | Schreiber et al. |
| 9,636,402 B2 | 5/2017 | Kaplan |
| 2002/0058854 A1 | 5/2002 | Reed et al. |
| 2002/0169354 A1 | 11/2002 | Munro, III |
| 2002/0180096 A1 | 12/2002 | Karl et al. |
| 2003/0064965 A1 | 4/2003 | Richter |
| 2003/0084988 A1 | 5/2003 | Terwilliger et al. |
| 2003/0088140 A1 | 5/2003 | Terwilliger et al. |
| 2003/0088141 A1 | 5/2003 | Terwilliger et al. |
| 2003/0088144 A1 | 5/2003 | Terwilliger et al. |
| 2003/0092958 A1 | 5/2003 | Terwilliger et al. |
| 2003/0097035 A1 | 5/2003 | Tucker |
| 2003/0171637 A1 | 9/2003 | Terwilliger et al. |
| 2004/0019381 A1 | 1/2004 | Pflueger |
| 2005/0038312 A1 | 2/2005 | Green |
| 2005/0159636 A1 | 7/2005 | Tarone |
| 2005/0267319 A1 | 12/2005 | White et al. |
| 2009/0171996 A1 | 7/2009 | Laxminarayanan |
| 2009/0193764 A1 | 8/2009 | Elliott |
| 2009/0223851 A1 | 9/2009 | Jacobs |

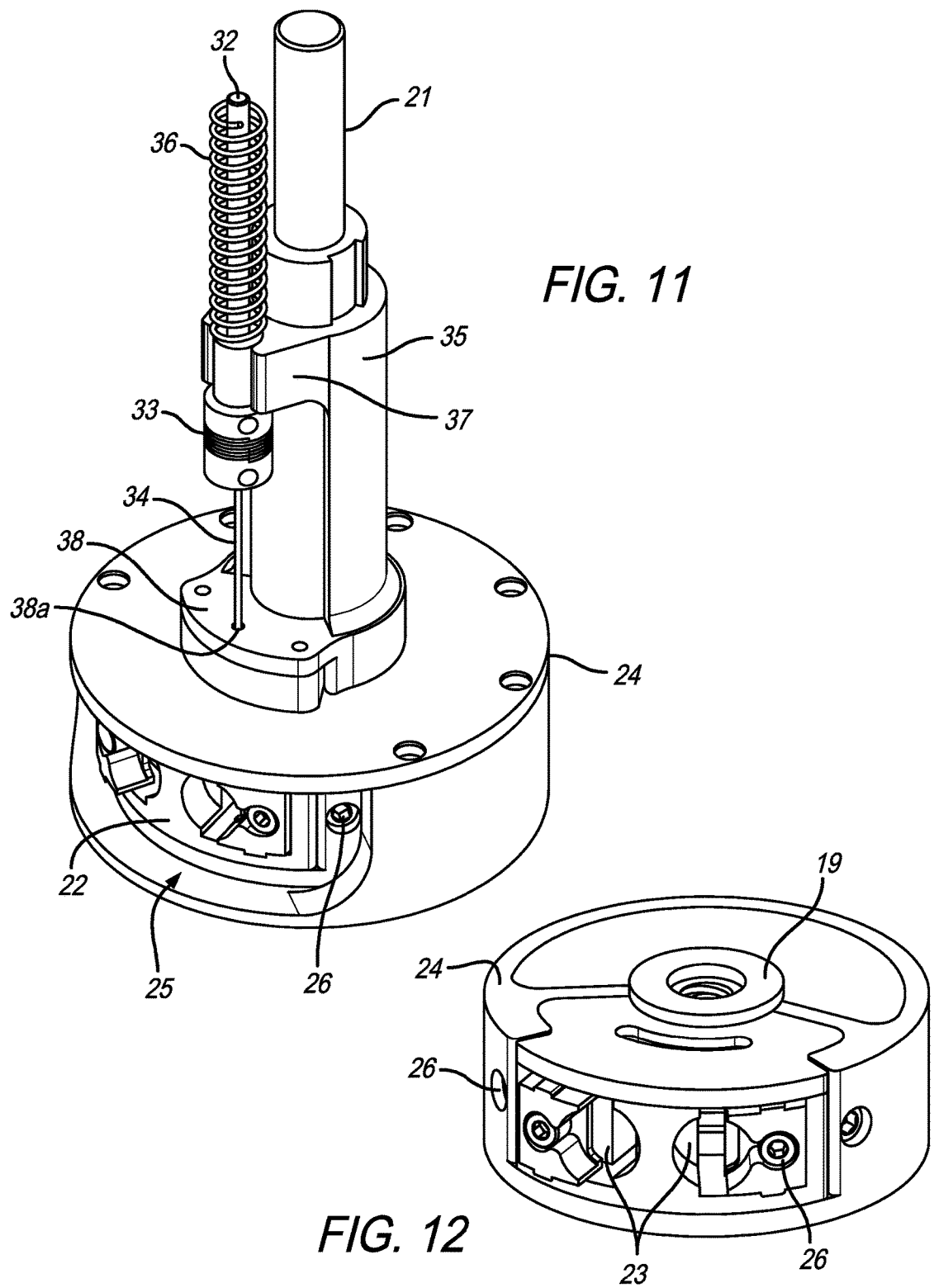

DEVICE FOR LOADING BRACHYTHERAPY SEEDS INTO IMPLANTATION SLEEVES

CROSS-REFERENCE TO RELATED APPLICATIONS

This application claims the benefit of U.S. Provisional Application No. 62/580,837 filed Nov. 2, 2017.

FIELD OF INVENTION

This invention relates generally to a device for loading seeds and spacers into brachytherapy implantation sleeves. This invention relates particularly to a loader that easily switches from one pellet cartridge to another, and displays the sequence during loading.

BACKGROUND

Brachytherapy is the treatment of cancer by the insertion of radioactive implants directly into the tissue near the tumor. The implants are minute radioactive pellets known as seeds. The seeds and, optionally, non-radioactive pellets known as spacers, are lined up end-to-end in strands that are held together in a sleeve until implant. The pellets are held in the sleeve, which is placed in a needle and secured there by plugging the end with bone wax. The loaded sleeve is then inserted into the patient's tissue at the desired location.

Seeds of a given radioactive species and dosage are provided in a magazine, which in turn is held in a shielded case to protect humans from excess radiation exposure before and during the implant procedure. The seeds are extracted from the magazine and inserted into the sleeve. A variety of seed loaders exist for this purpose. The sleeve is inserted into a patient using a needle.

The amount of radiation to be delivered to the patient and placement pattern of the sleeves are determined in advance of the treatment. The sleeves are prepared accordingly, either pre-loaded per the irradiation plan before treatment or as the insertions are carried out during treatment. Once the treatment starts, the physician may determine that a different dosage or placement is needed, and the seeds and spacers need to be rearranged.

Loading a sleeve is a delicate process, and re-arranging the seeds and spacers as they go into a sleeve is very difficult. It would be desirable to have a loader that makes it easy to load seeds and spacers, and to easily rearrange them prior to inserting them into the sleeve.

SUMMARY OF THE INVENTION

This invention is a device for loading brachytherapy seeds and spacers into a sleeve. The device may hold two or more seed or spacer cartridges of different radioactive species and dosage. The user rotates a selector for selecting a desired cartridge and, with each depression of a spring-biased plunger, pushes a desired seed or spacer into a channel in an inspection area. The process is repeated for the desired number and order of seeds and spacers in sequence to form a strand. The seeds and spacers can be seen in the channel with the unaided eye through a transparent view window. The view window is part of a hinged door that can be opened and the sequence of the seeds and spacers rearranged with forceps, if necessary. Once the strand is arranged as desired, it is pushed into a sleeve in a removable sleeve holder. Optionally the sleeve may be formed with pre-spaced compartments to hold each pellet in a spaced relationship with the other seeds as they are pushed into place. At the time of radiation treatment, the filled sleeve is removed from the sleeve holder and implanted into patient using a needle.

BRIEF DESCRIPTION OF THE DRAWINGS

FIG. 11 is a top perspective view of the turret assembly of the first embodiment of the present invention.
FIG. 12 is a top perspective view of the turret of the first embodiment of the present invention.

DETAILED DESCRIPTION OF THE INVENTION

Figure 1:
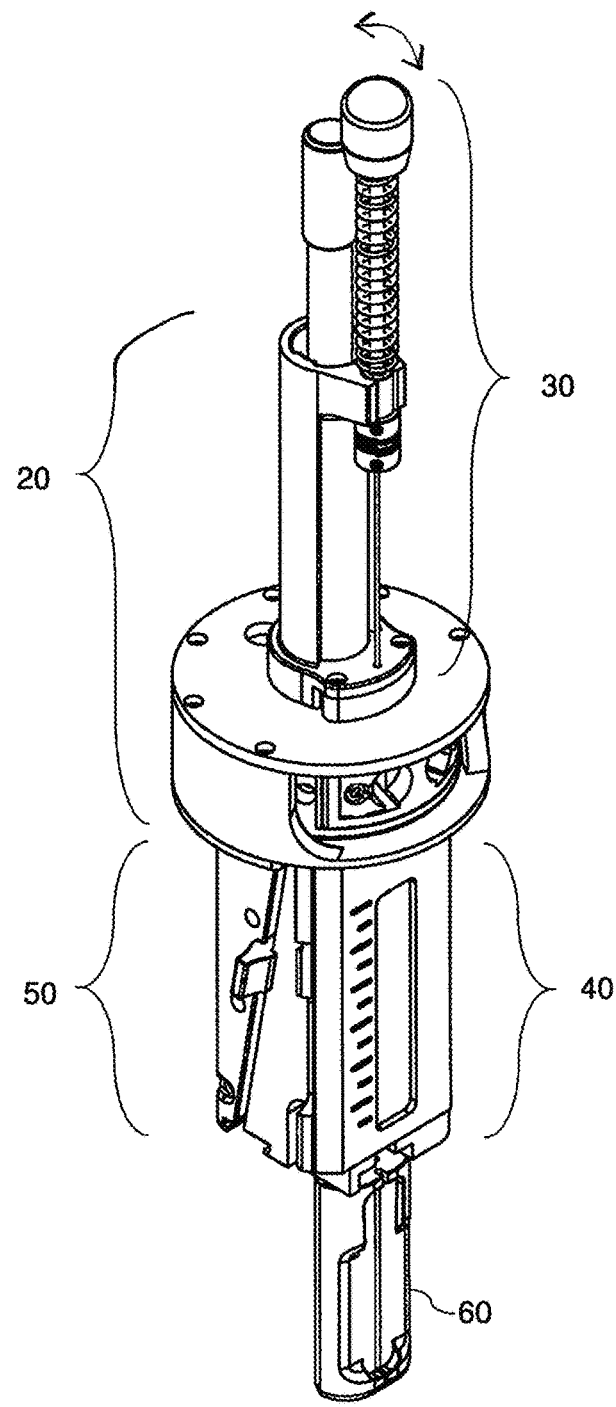
FIG. 1 is a top perspective view of a first embodiment of the present invention.
Figure 2:
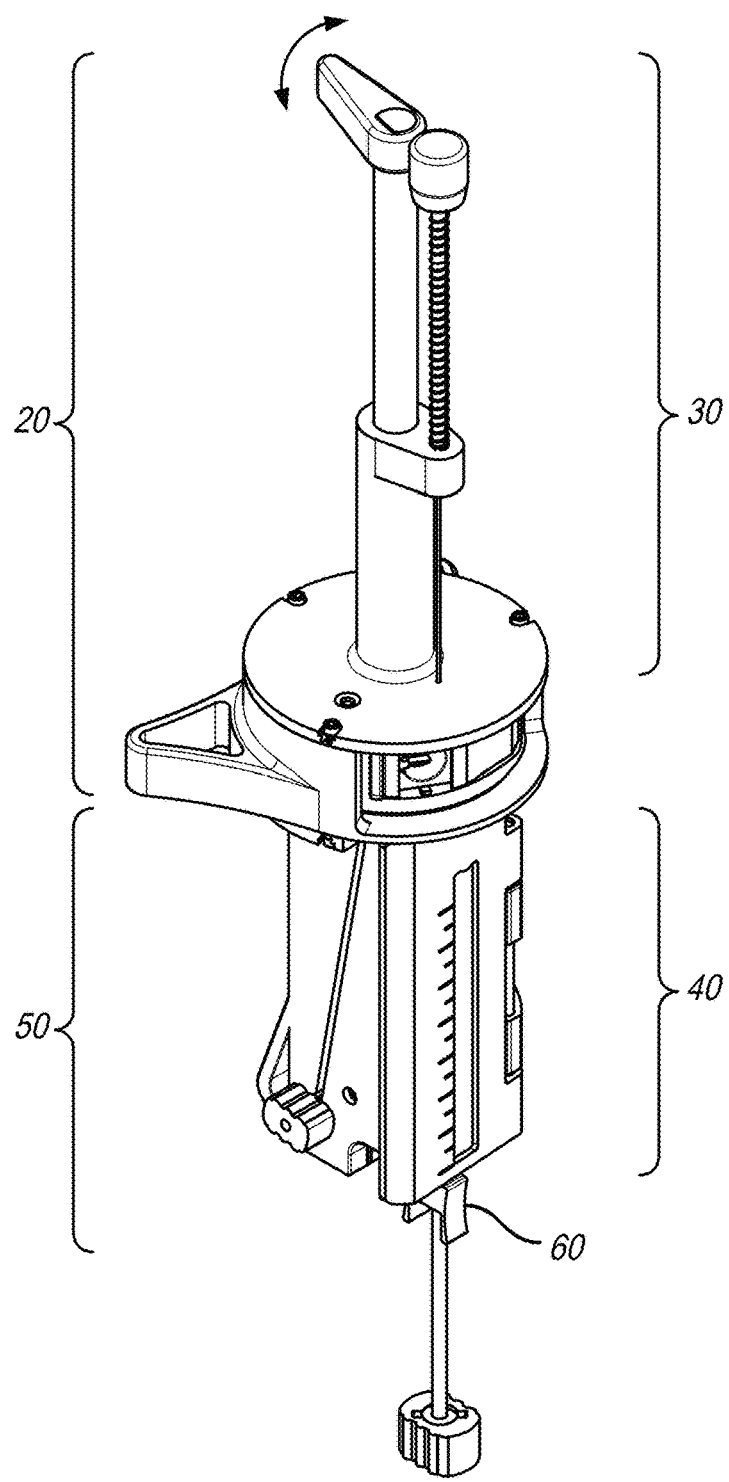
FIG. 2 is a top perspective view of a second embodiment of the present invention.
Figure 3:
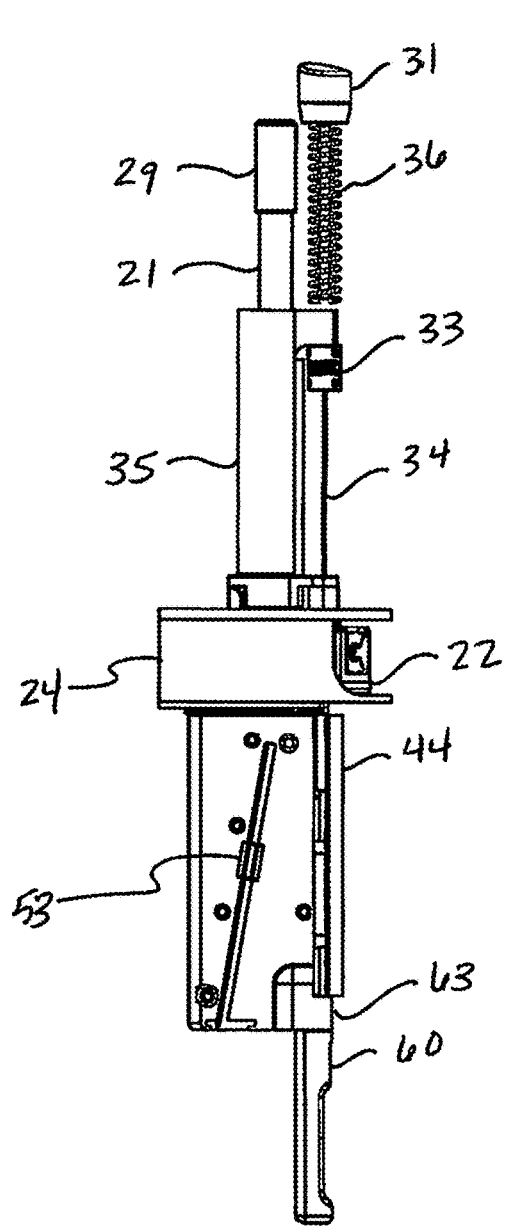
FIG. 3 is a left side view of the device in FIG. 1.
Figure 4:
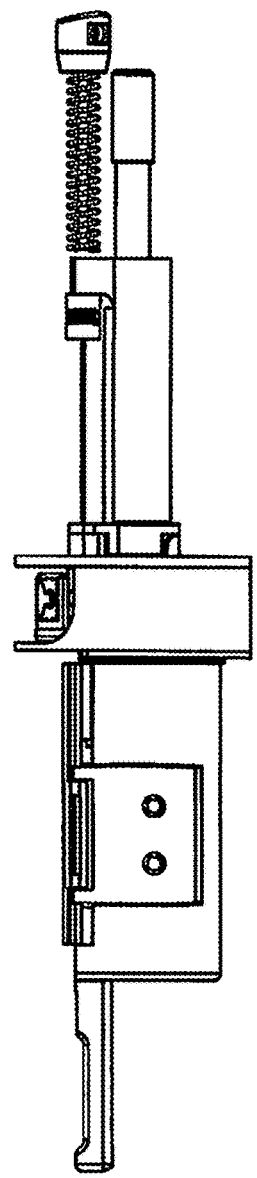
FIG. 4 is a right side view of the device in FIG. 1.
Figure 5:
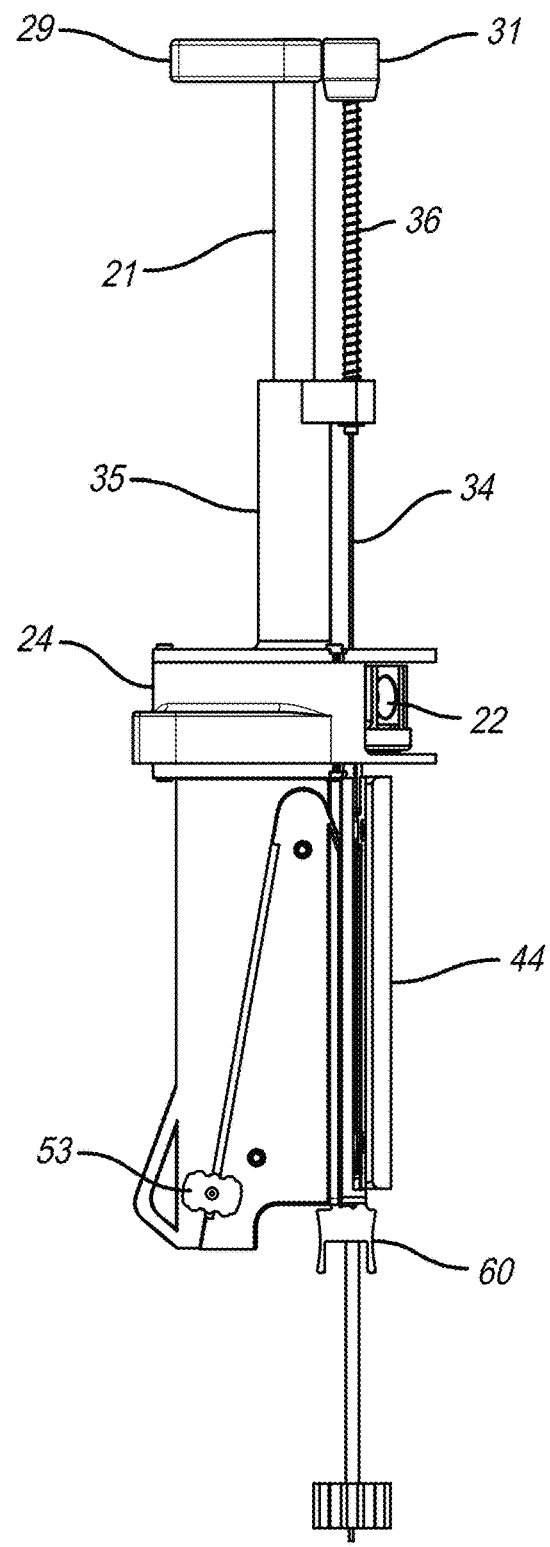
FIG. 5 is a left side view of the device in FIG. 1.
Figure 6:
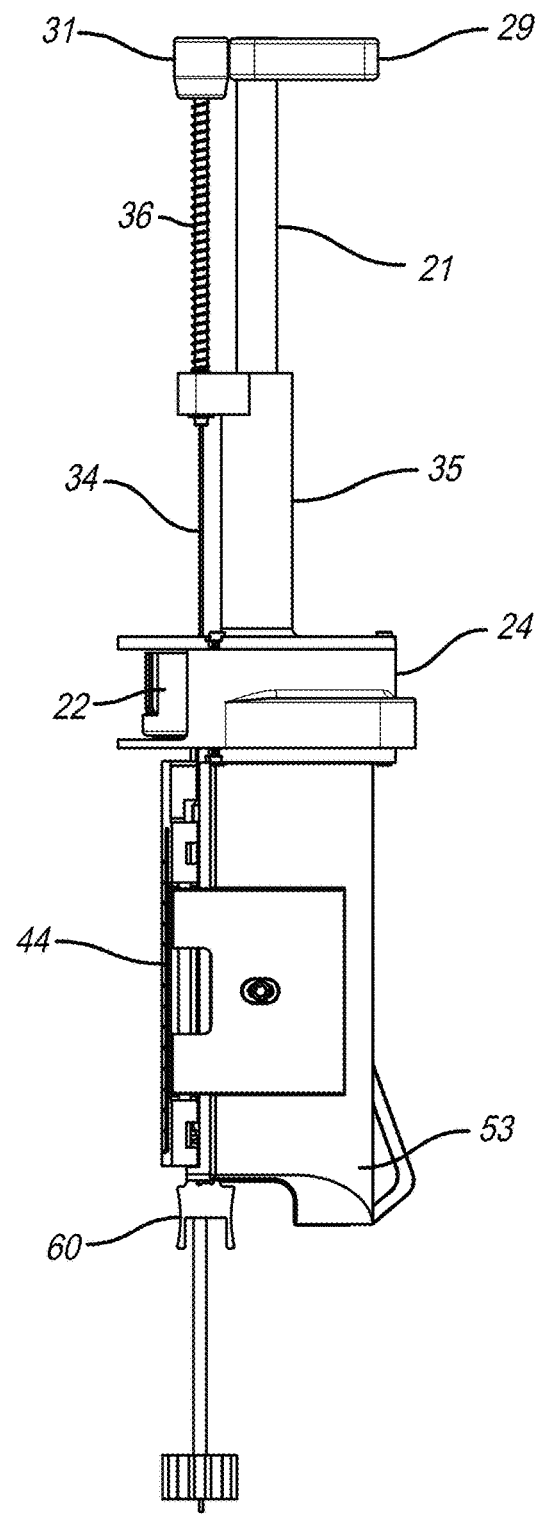
FIG. 6 is a right side view of the device in FIG. 1.
Figure 7:
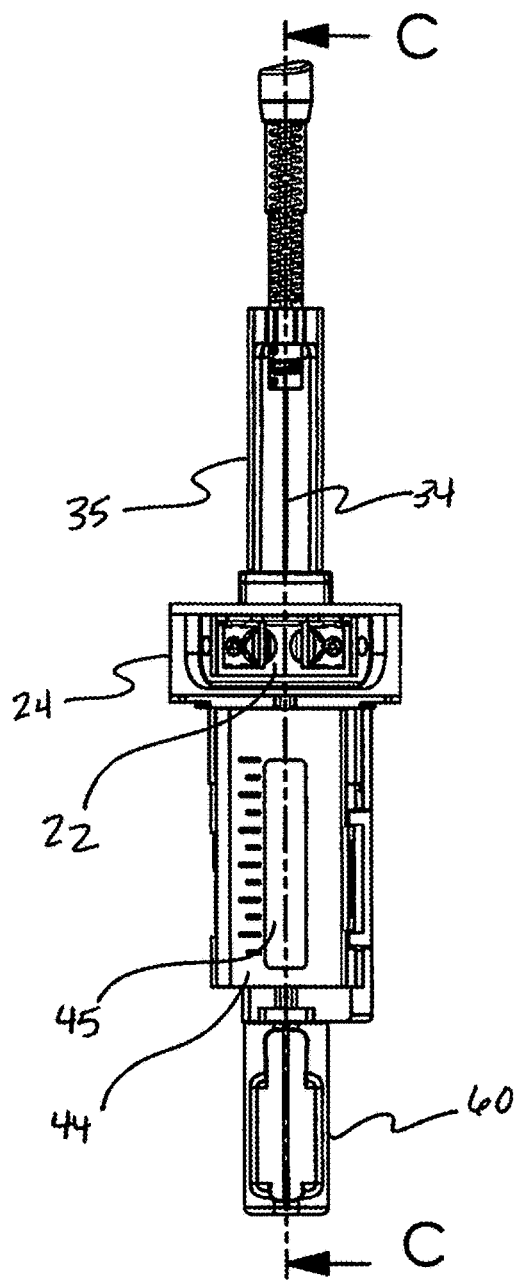
FIG. 7 is a front view of the device in FIG. 1.
Figure 8:
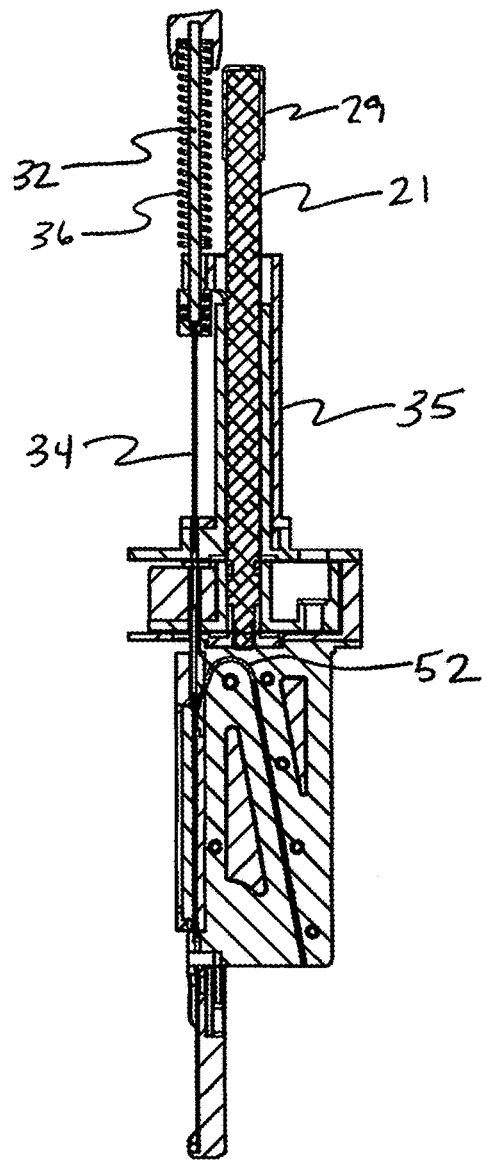
FIG. 8 is a cross-section view along line C-C of FIG. 7.
Figure 9:
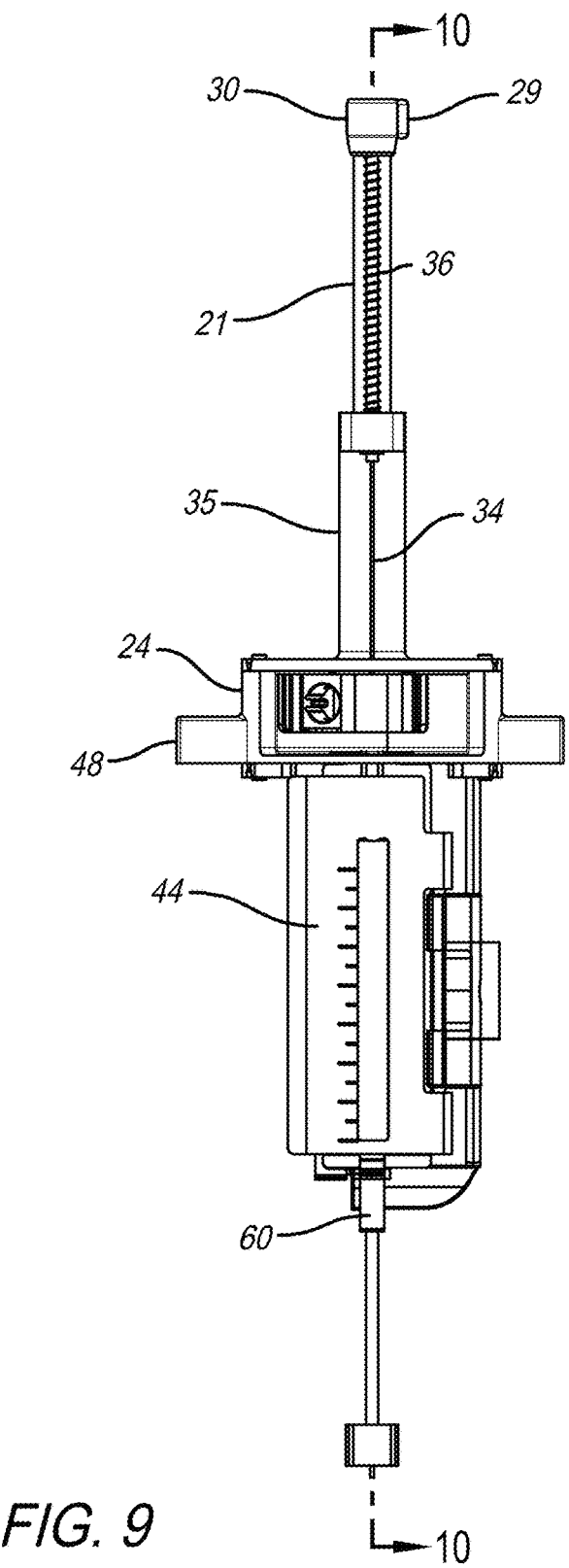
FIG. 9 is a front view of the device in FIG. 2.
Figure 10:
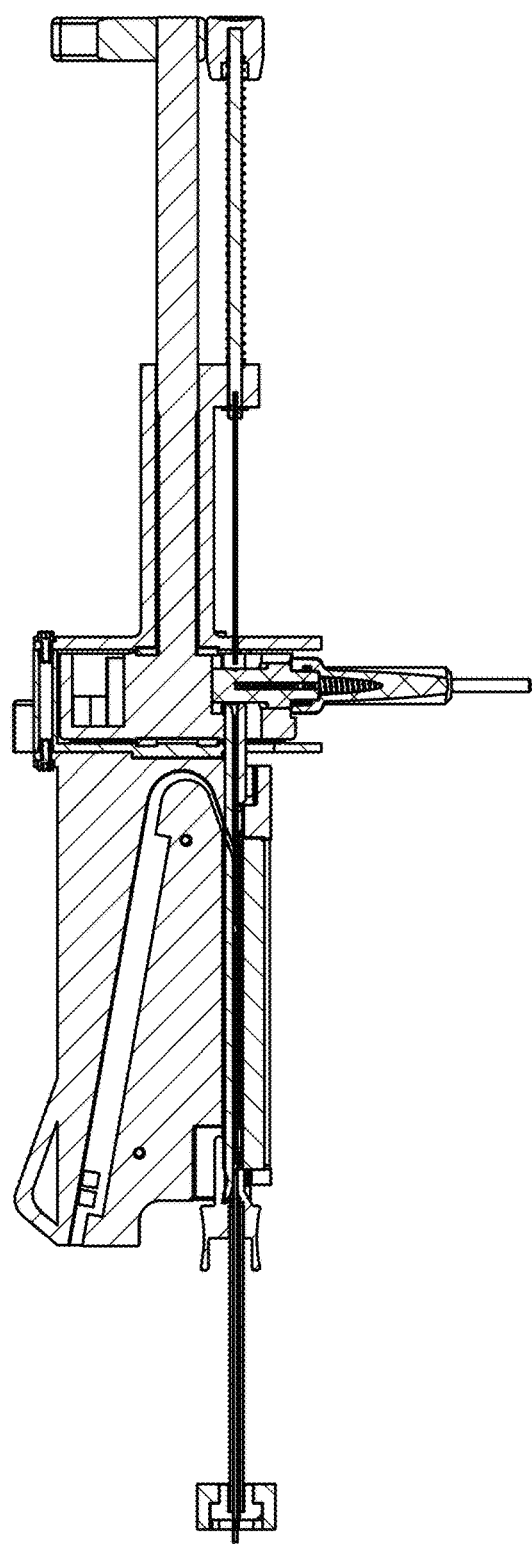
FIG. 10 is a cross-section view along line D-D of FIG. 9.

The invention is a device for loading brachytherapy seeds and spacers from one or more cartridges 9 into an implantable insertion sleeve 62. The device is configured to be hand-held or removably affixed to a table or countertop. One embodiment has stand legs 48 to support the device on a table or countertop. Alternatively the device can be supported on a table or countertop with a jig (not shown).

The device has four assemblies that cooperate to arrange and load the seeds and spacers, which are alternatively and collectively referred to herein as pellets 7. A turret assembly 20 enables a user to select a desired cartridge 9. A plunger assembly 30 pushes a pellet 7 from the cartridge 9 into a channel 41 in an inspection assembly 40. The inspection assembly 40 receives the pellets end-to-end and permits the user to view the strand 61 as it is being built. A strand pusher assembly 50 pushes the strand 61 into the sleeve 62 which is held in a removable sleeve holder 60. The sleeve 62 is a hollow tube, also known the art as a straw. The filled sleeve 62 is removed from the sleeve holder 60 and implanted into patient using a needle (not shown) at the time of radiation treatment. The passageway for the pellets' travel is in fluid communication between a first open end in the turret assembly through the inspection assembly and into the sleeve. Preferably the passageway is straight, but may have bends or curves. FIGS. 1-10 show two embodiments of the device with the assemblies connected to each other, along with the attached sleeve holder.

The device is modular so that several of the assemblies and subassemblies can be easily removed and replaced with parts having similar functions but different shapes and sizes, which permits the device to accommodate a wide variety of cartridges, pellets, and sleeves. For example, the pellets may be of different radioactive materials or of non-radioactive materials, the pellets may have different lengths and diameters, the sequence length may be longer or shorter, and the sleeves may be made of a variety of sleeve materials. The modularity in turn permits different types of treatment designs for pellet placement in different areas of the body.

The turret assembly 20 comprises a selector rod 21 fixed to the turret head 22, which is disposed in a rotatable relationship within a turret housing 24. See FIGS. 11, 12, 14, and 15. As used herein, a fixed relationship means that the parts are static relative to one another when connected, although fixed parts may be separable to permit easy replacement with similar parts. As used herein, a rotatable relationship means that the parts are rotatable relative to one another when connected. The rotatable parts may also be separable to permit easy replacement with similar parts.

The turret head 22 has two or more head apertures 23 along its perimeter to receive two or more cartridges 9. The turret housing 24 has at least one housing aperture 25 along its perimeter to permit the cartridges 9 to be inserted through the turret housing 24 into the turret head 22. The turret head 22 and turret housing 24 each have a top thru-slot 27 and a bottom thru-slot 28, respectively, that permit a plunger pin 34 to travel through the turret housing and turret head 24 into a cartridge 9 to eject a pellet into the inspection assembly, as described in more detail below. Optionally, adjustment screws 26 allow for individual depth adjustment of each cartridge 9.

Figure 34:
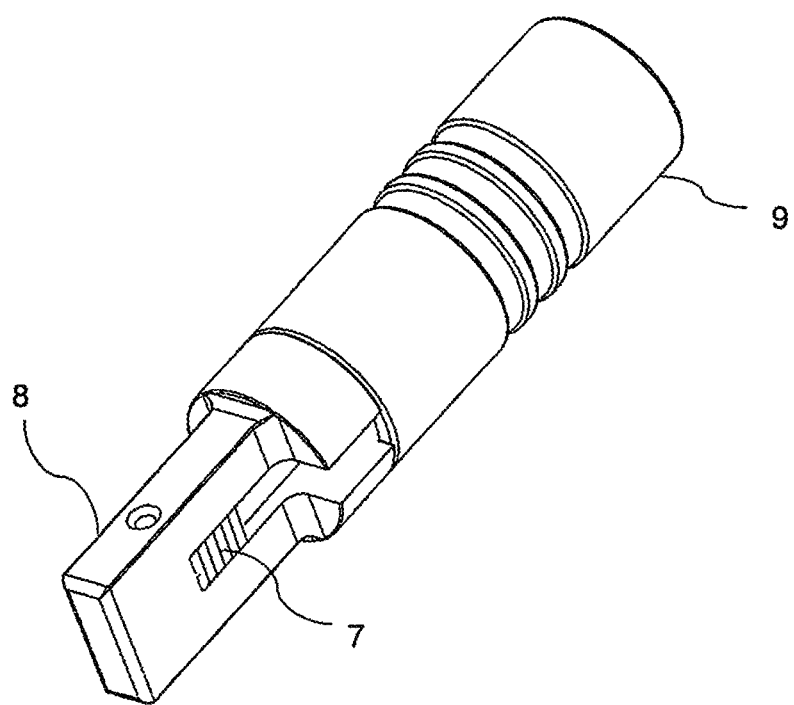
FIG. 34 is a perspective view of a Mick® cartridge of the prior art.

The head apertures 23 are shaped to mate with the desired cartridge 9. Mick® cartridges, shown in FIG. 34, are cylindrical and commercially available. The magazine 8 holding the pellets 7 inside the Mick® cartridge has a rectangular cross section. In the preferred embodiment the cartridges are cylindrical and are mated to circular head apertures 23 in the turret head 22, as shown in FIGS. 11, 12, 14, and 15. In other embodiments the head apertures 23 have a rectangular or square shape to mate with cartridges having rectangular or square cross-section, respectively. Turret heads 22 are interchangeable with in the turret housing 24, making the device easily compatible with multiple shapes and types of cartridges.

The turret assembly 20 and plunger assembly 30 cooperate to enable the plunger assembly 30 to be rotated relative to the turret head 22. A low friction bushing 19 may be employed at the interface of the turret head 22 and the turret housing 24 to enable quick rotation without causing wear to the surfaces. Visual indicators such as hash marks may be employed to show when the plunger pin 34 is properly aligned over the cartridge 9. A detent mechanism may be employed at the interface of the turret head 22 and the turret housing 24 to assure that the plunger pin 34 is properly aligned over the cartridge 9 and to give a tactile indication to the user that alignment is proper.

The plunger assembly 30 comprises a hollow plunger tower 35 that is fixed to or integral with the turret housing 24. In one embodiment shown in FIG. 11, the plunger tower 35 is attached to the turret housing at a base 38. In a second embodiment shown in FIG. 14, the plunger tower 35 is attached to the turret housing without a base 38. The turret housing 24 has a thru-hole 38a to receive the plunger pin 34, which in turn will eject a pellet from the selected cartridge. In the embodiment with the base, the base has a thru-hole co-axial with the thru-hole in the turret housing to receive the plunger pin 34. In the preferred embodiment the plunger tower 35 is co-axially aligned with the turret head 24, but in other embodiments it may be off-center. See FIG. 6. The plunger assembly 30 further comprises a guide collar 37 to hold a plunger subassembly 39 along an axis that is offset from, but parallel to, the axis of the plunger tower, and that is aligned with the channel 41 in the inspection assembly 40. See FIG. 8.

Figure 17:
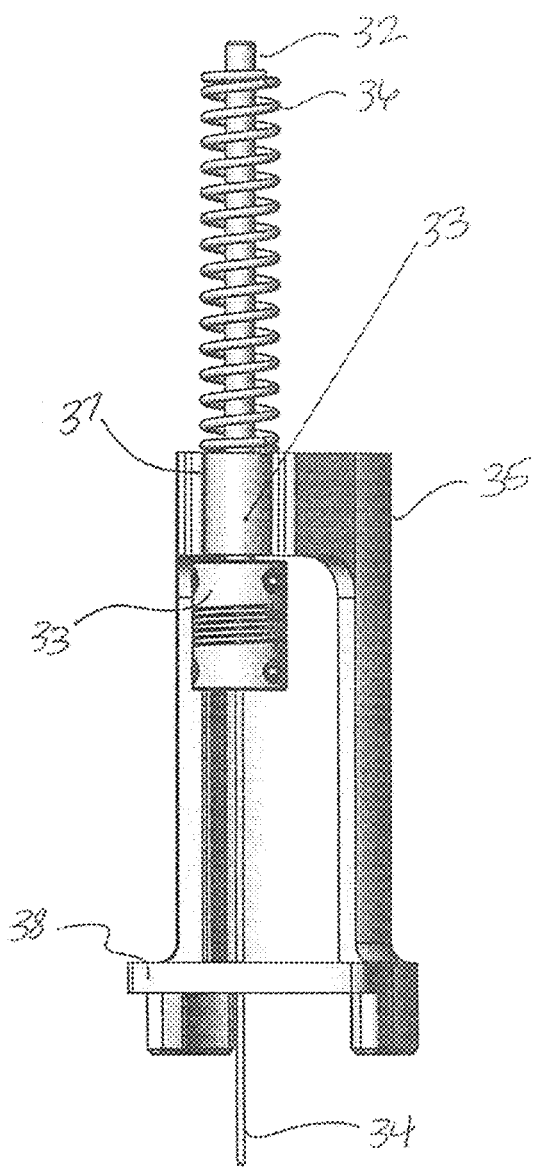
FIG. 17 is a front view of the plunger assembly of the first embodiment of the present invention.
Figure 18:
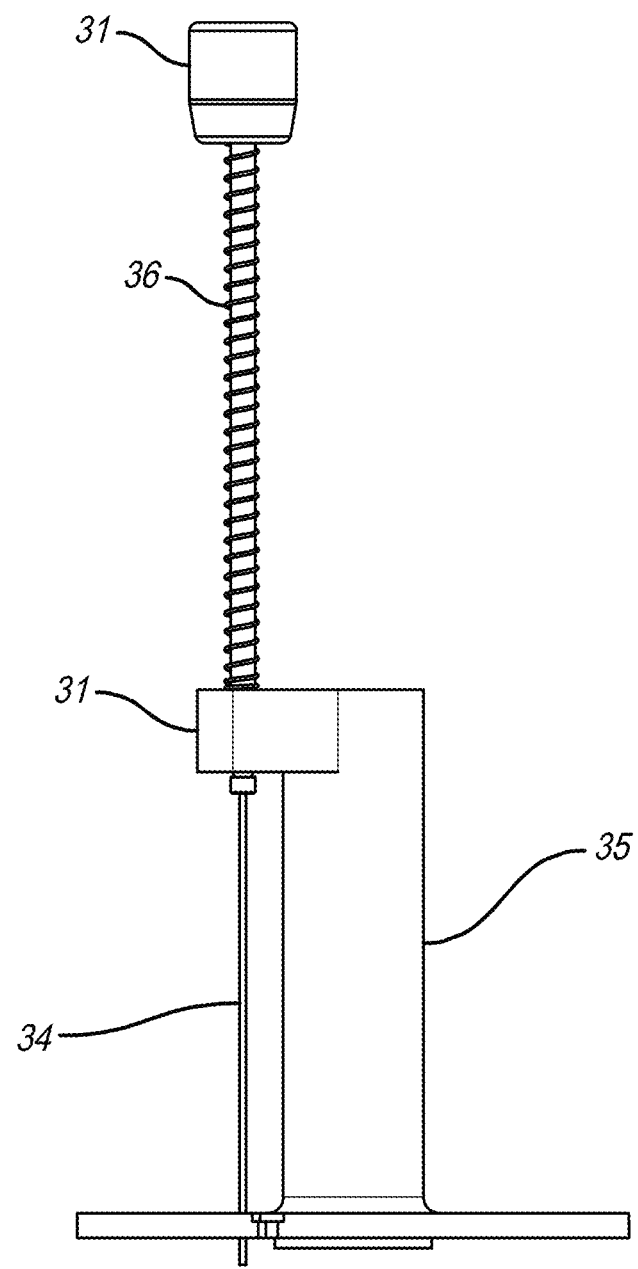
FIG. 18 is a front view of the plunger assembly of the second embodiment of the present invention.
Figure 20:
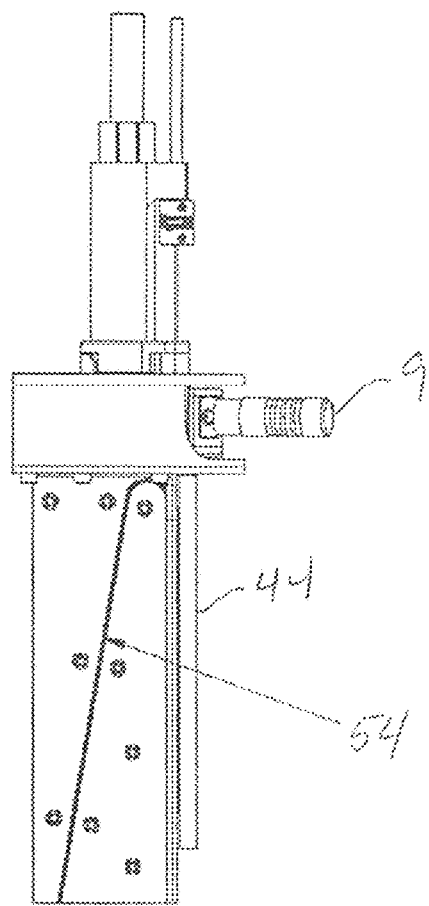
FIG. 20 is partial side view of the first embodiment of the present invention.
Figure 21:
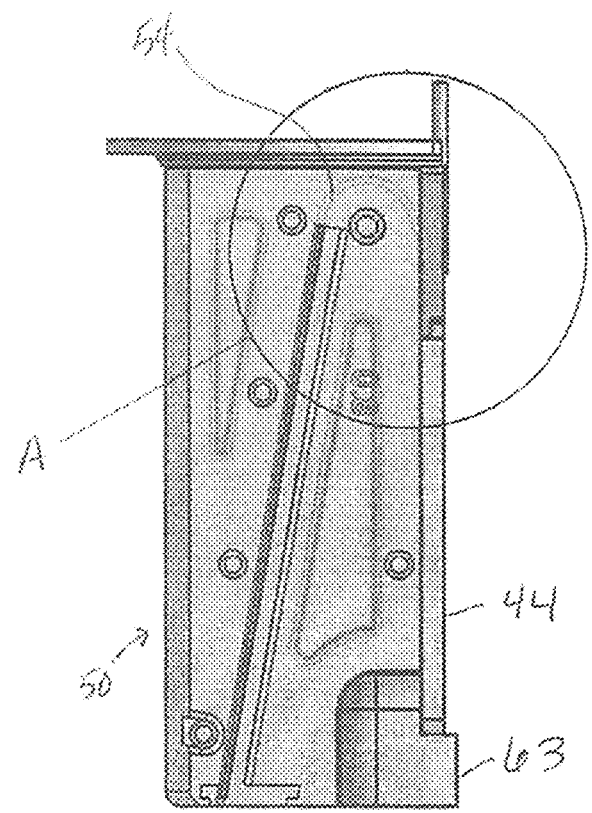
FIG. 21 is a close-up side view of the strand pusher assembly.

The plunger subassembly 30 comprises a plunger 32, a coupler 33, a plunger pin 34, and a spring 36, all co-axially aligned and held in fixed relationship to the plunger tower 35 by the guide collar 37. See FIGS. 17 and 18. The plunger 32 is spring biased in an "up" position, with the plunger pin 34 retracted from the cartridge. The plunger subassembly optionally and preferably also comprises a plunger cap 31 that provides a surface for a user's finger to have certain purchase on the plunger. The coupler 33 may hold the plunger at a set resting depth, or may enable the resting depth to be adjusted by about 1-4 mm. A coupler 33 also allows easy replacement of the plunger pin 34.

Figure 13:
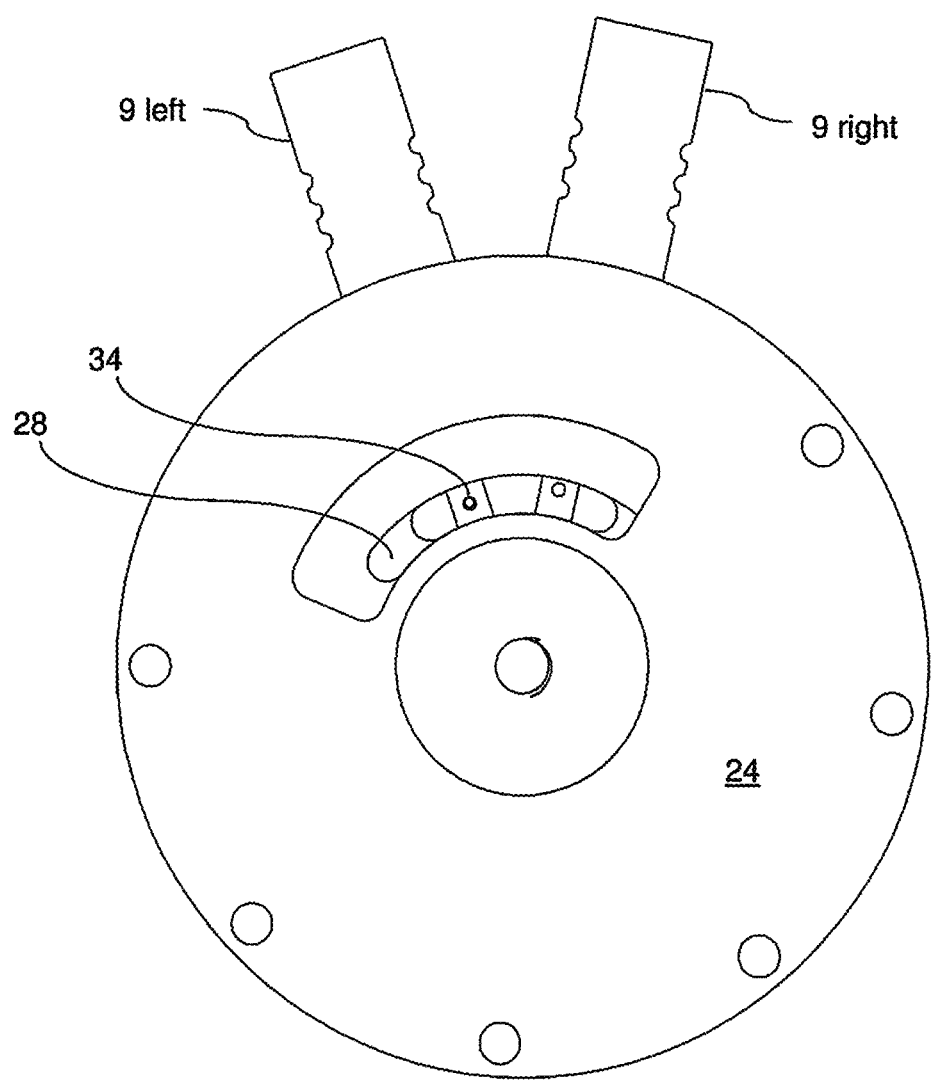
FIG. 13 is a bottom perspective view of the turret of the second embodiment of the present invention.
Figure 14:
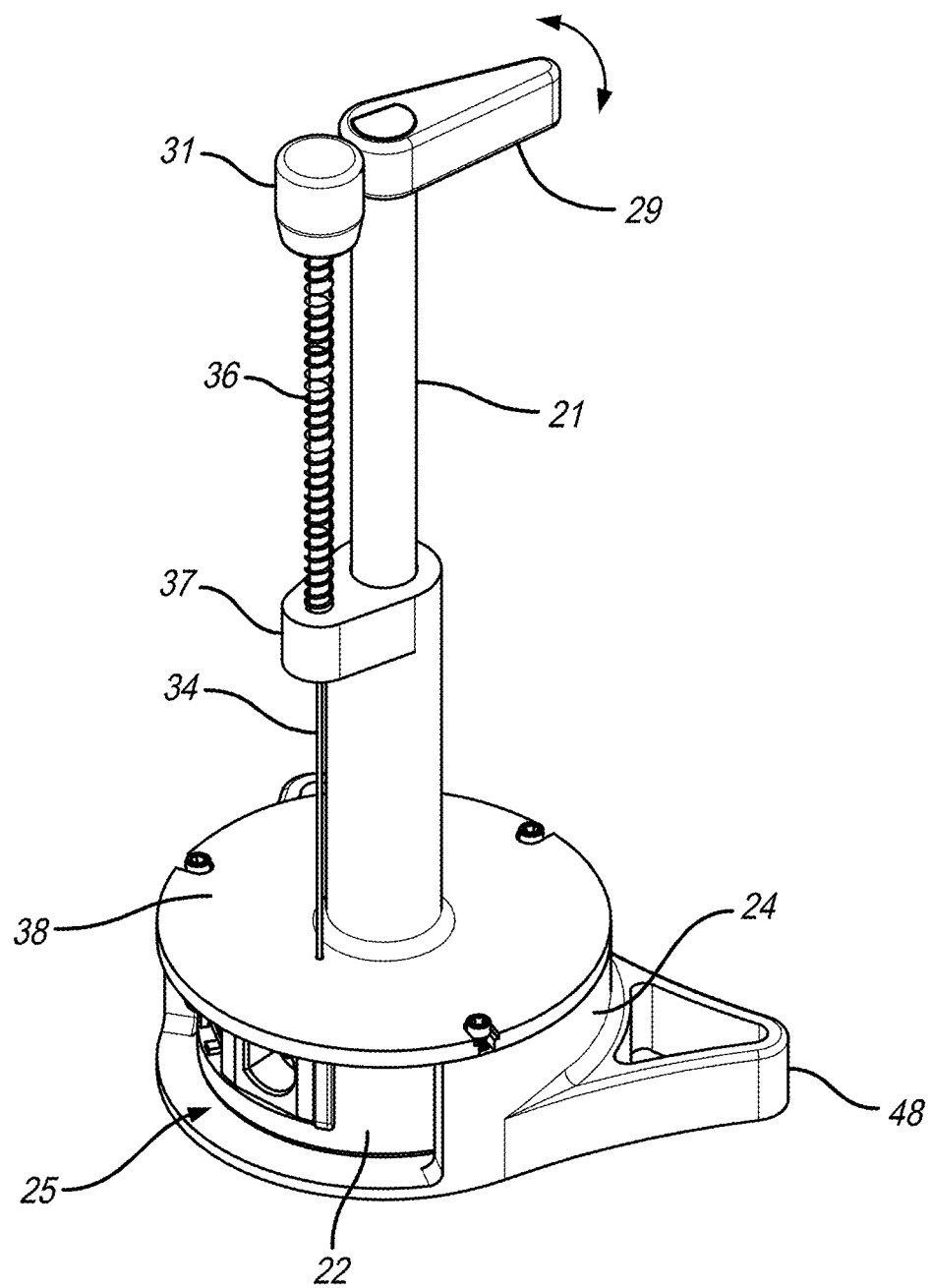
FIG. 14 is a top perspective view of the turret assembly of the second embodiment of the present invention.
Figure 15:
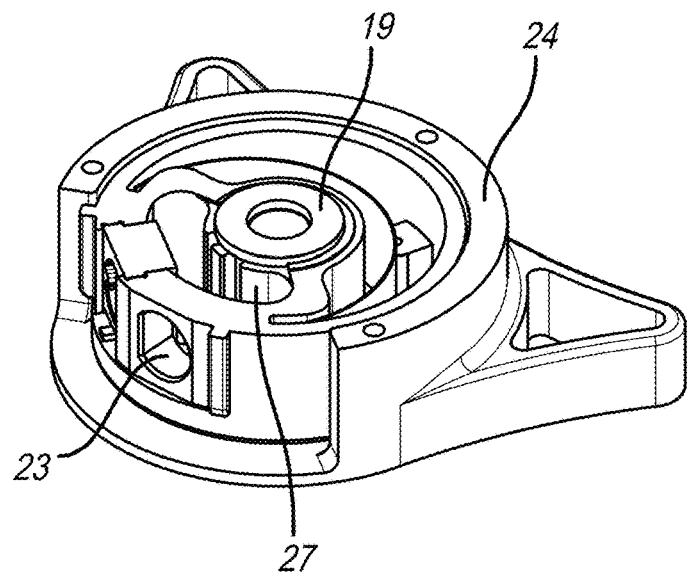
FIG. 15 is a top perspective view of the turret of the second embodiment of the present invention.
Figure 16:
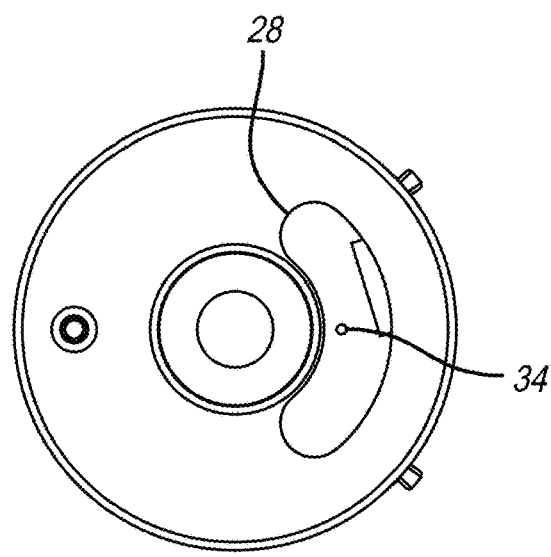
FIG. 16 is a bottom perspective view of the turret of the second embodiment of the present invention.
Figure 30:
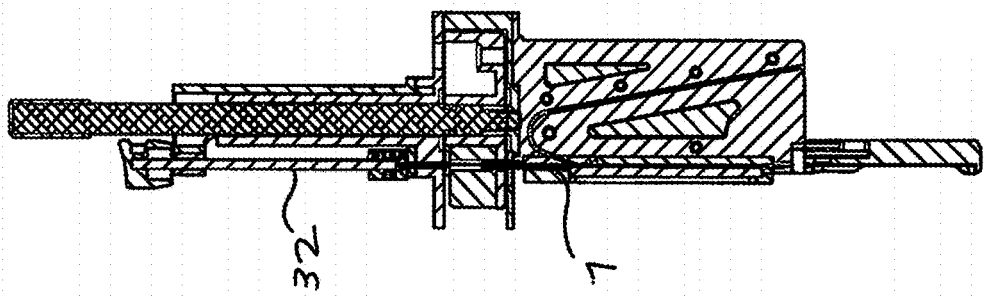
FIG. 30 is a front cross-section of the device with Mick® cartridges inserted and the plunger in the up position.
Figure 29:
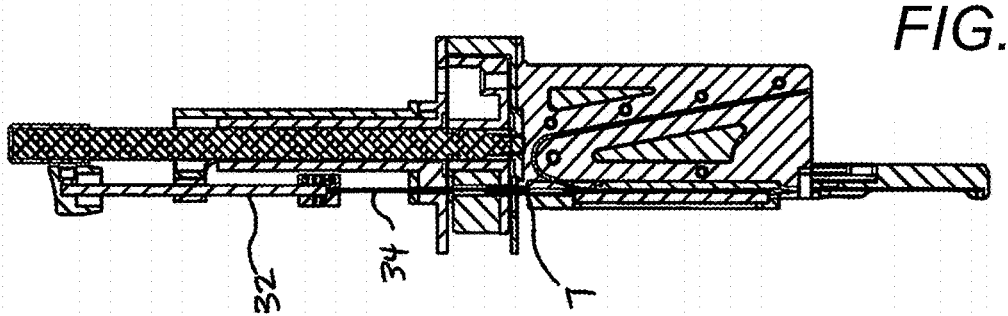
FIG. 29 is a front cross-section of the device with Mick® cartridges inserted and the plunger in the up position.
Figure 28:
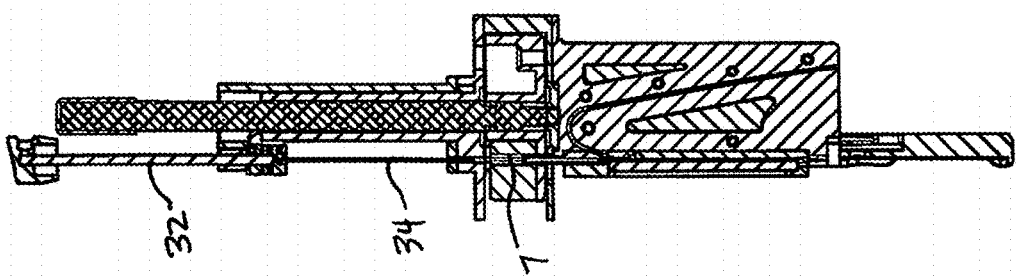
FIG. 28 is a front cross-section of the device with Mick® cartridges inserted and the plunger in the up position.

The selector rod 21 is co-axially aligned in the plunger tower 35 and rotates within the plunger tower to turn the turret head 22 to align the desired cartridge over the channel 41 in the inspection assembly 40. FIG. 13 shows the bottom view of the turret head 22 rotated to select the cartridge 9a on the right in a first embodiment of the device. FIG. 16 shows the bottom view of the turret head 22 rotated to select the cartridge 9a on the right in a second embodiment of the device. The selector rod 21 optionally and preferably also comprises a selector rod cap 29 that provides a lever or knurled surface for a user's fingers to more easily grip the selector rod. The user rotates the selector rod 21 for selecting a desired cartridge, as shown by the arrow in FIGS. 1 and 2. With each depression of a spring-biased plunger 32, the user pushes a desired seed or spacer into a channel 41 in an inspection area. FIGS. 28-30 show cross-sectional views of the device as the plunger is pressed down, moving the plunger pin 34 from the turret housing 24 through the turret head 22, the cartridge, and finally into the channel 41 of the inspection assembly 40. The full stroke of the plunger places the pellet at a distance from the selected cartridge sufficiently far from the cartridge body that moving the turret will not contact or damage the pellet or selection mechanism. The spring forces the plunger subassembly 39 back to its resting position and the process of rotation and pellet ejection is repeated for the desired number and order of seeds and spacers in sequence to form a strand. Alternatively, the plunger may be moved and retracted by means other than a spring, such as manually using a detent system.

Figure 19:
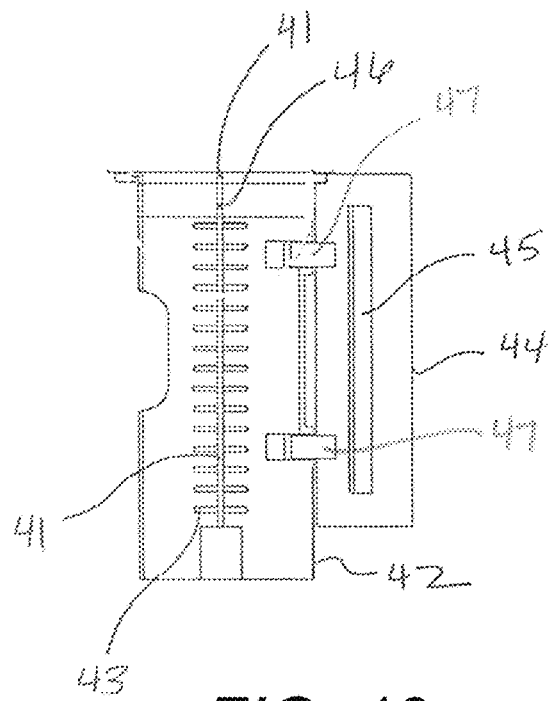
FIG. 19 is a front view of the inspection assembly of the first embodiment of the present invention with the door open.
Figure 27:
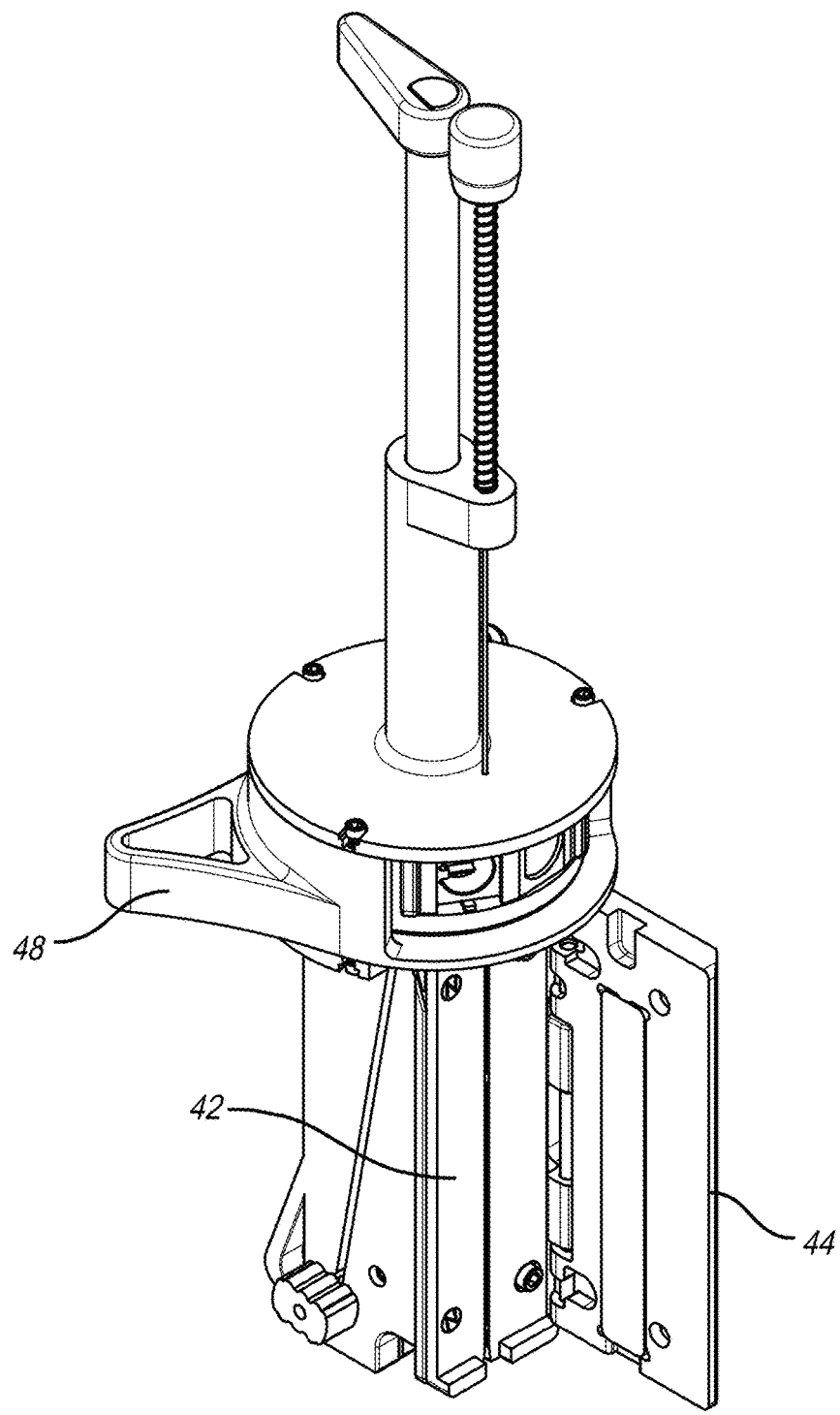
FIG. 27 is a top perspective view of a portion of the second embodiment of the device with Mick® cartridges inserted and the door open.

The inspection assembly 40 is fixed to the turret housing 24. It comprises a flat plate 42 into which a channel 41 is indented to receive the pellets. See FIGS. 19 and 27. Optionally, the plate has forceps slots 43, which are grooves that are sized and oriented to facilitate forceps picking up an individual pellet from the channel 41. As used herein, forceps refers to any type of device that can move a single seed, including for example forceps, tweezers, pincers, or a pick. The slots 42 enable the tips of the forceps to fit into the slot below the surface of the plate 42, which helps secure the aim and grip on the tiny pellet while it is in the channel 42. The forceps slots 43 may be indentations in the plate that do not go all the way through the thickness of the plate 42, or they may be through-holes. The flat plate 42 also comprises a thru-hole 46 that is in communication with the strand-pusher assembly 50, as described in more detail below.

Figure 24:
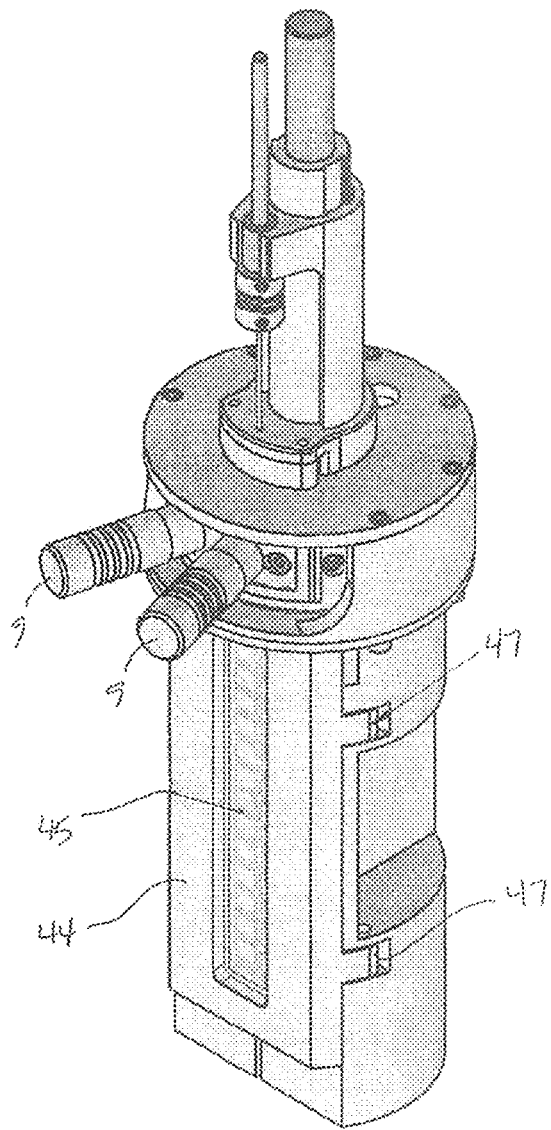
FIG. 24 is a top perspective view of a portion of the first embodiment of the device with Mick® cartridges inserted and the door closed.
Figure 25:
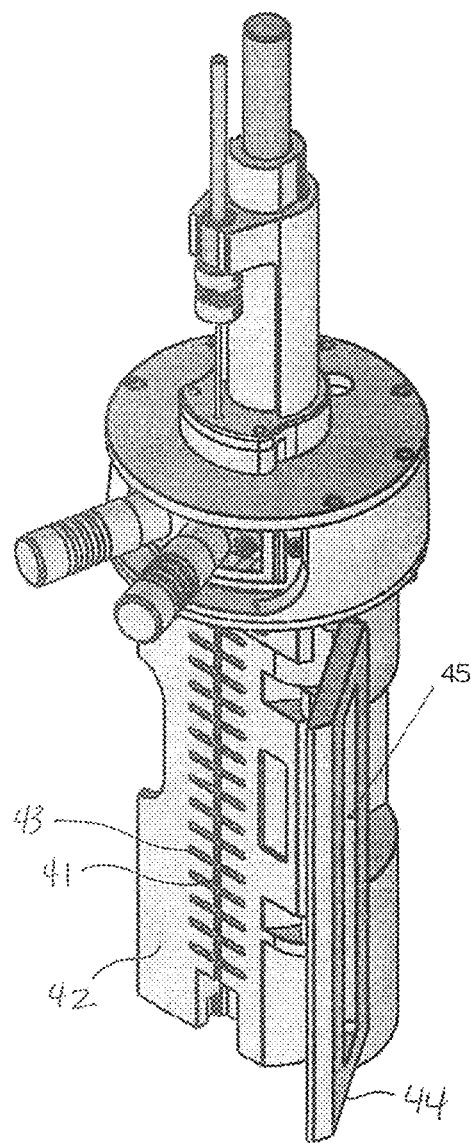
FIG. 25 is a top perspective view of a portion of the first embodiment of the device with Mick® cartridges inserted and the door open.
Figure 26:
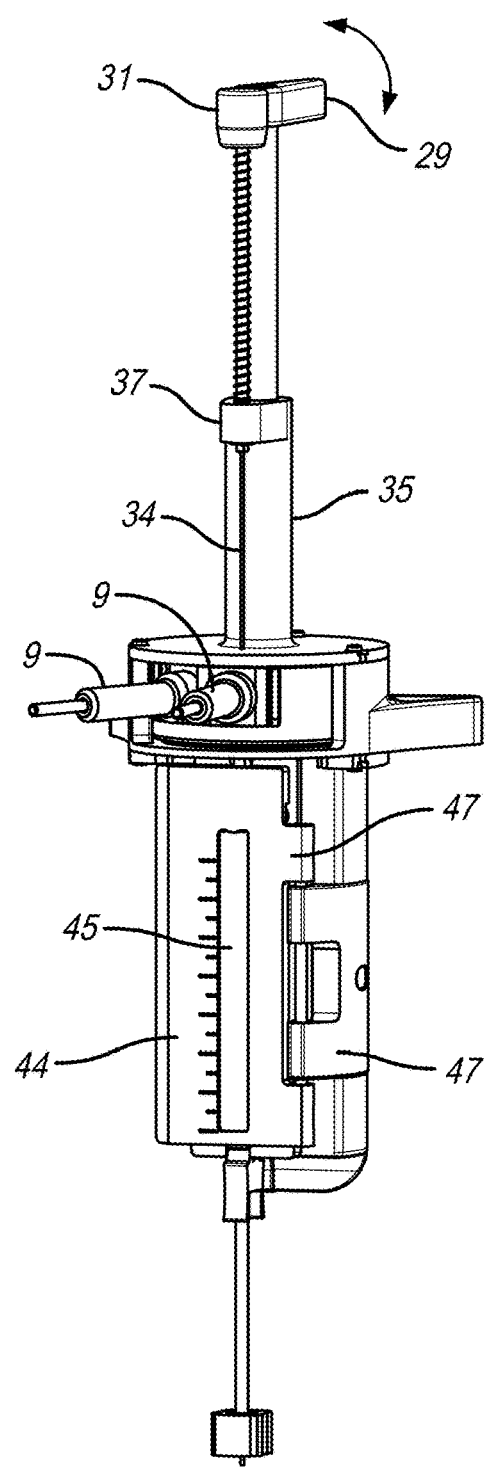
FIG. 26 is a top perspective view of a portion of the second embodiment of the device with Mick® cartridges inserted and the door closed.

The inspection assembly 40 further comprises a hinged door 44 which encloses the channel and the sequence when it is closed so that the pellets cannot fall out of the channel 41. The door 44 has a transparent portion 45 permits the user to see the seeds and spacers with the unaided eye while the door 44 is closed, as the strand is being built. The transparent portion is preferably a slot window, as shown in FIGS. 24-26, or the transparent portion may as large as the entire door 44. The door may have markings 49 for calibrations.

The door 44 is attached to the plate 42 at hinges 47. When the door is closed the channel is enclosed and any pellets therein are held securely. The user can open the door 44 to access the pellets in the channel 41, and use forceps (not shown) to remove a seed or spacer or rearrange the sequence before the strand is pushed into the sleeve 62. This enables the user to adjust the radiation treatment plan intraoperatively, with real-time creation of each strand. The user then closes the door and continues building the sequence of seeds and spacers.

Figure 22:
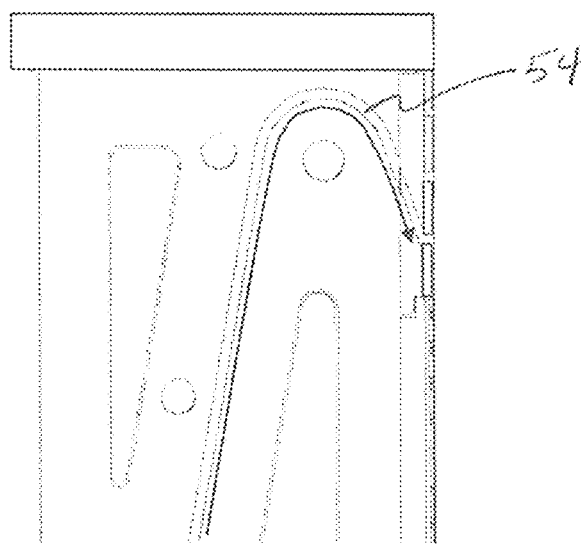
FIG. 22 is a close-up view of area A indicated in FIG. 21.
Figure 23:
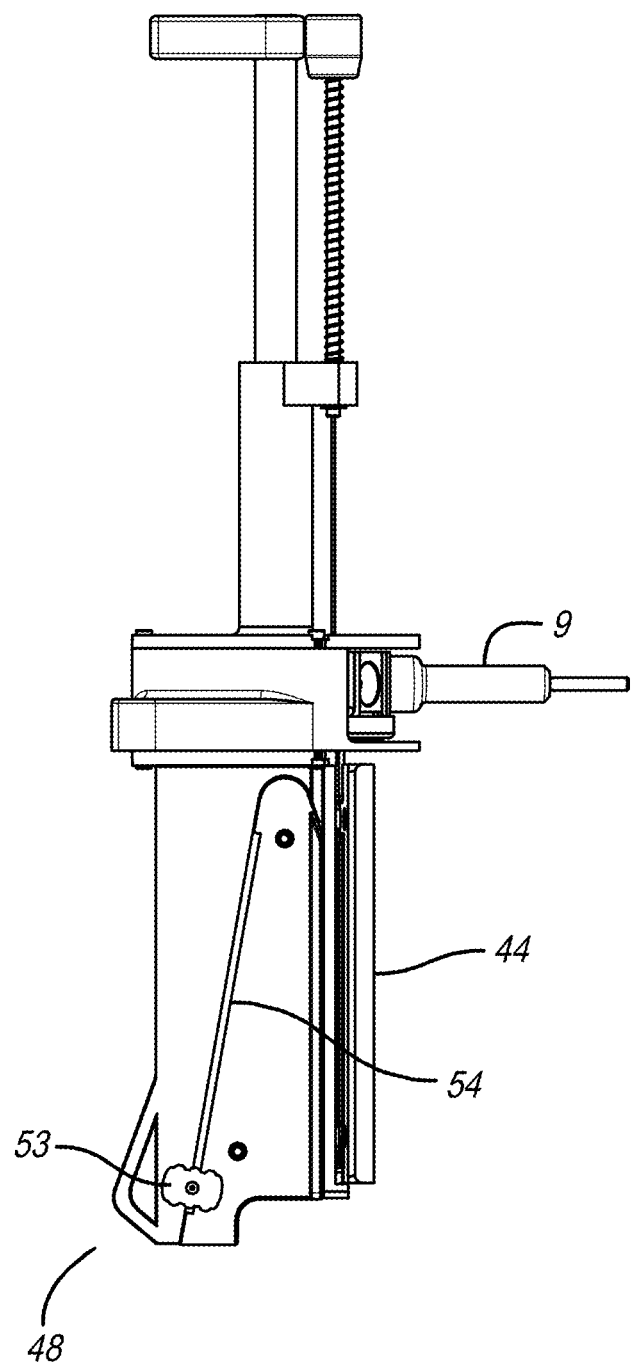
FIG. 23 is partial side view of the second embodiment of the present invention.

A strand-pusher assembly 50 is fixed to the inspection assembly 40. See FIGS. 1 and 2. The strand-pusher assembly 50 uses a mechanism to physically push the sequence into the awaiting sleeve 62 in the sleeve holder 60. In a preferred embodiment, the strand-pusher assembly 50 comprises a dispensing wire 51 seated in an arcuate channel 52. See FIGS. 20-23. The path of the wire is indicated by the arrow in FIG. 22. The dispensing wire 51 is deformable, resilient and flexible, and is preferably nitinol. A tab 53 is fixed to the wire 51 through a tab slot 54 and is used to push the wire 51 along the channel 52 and through the thru-hole 46 of the inspection plate 42. By moving the tab 53, the wire 51 bends in the arcuate channel and contacts the proximate end of the sequence that is in the inspection channel 41. Pushing the tab 53 further forces the wire 51 to ease the sequence into the awaiting sleeve 62 in the sleeve holder 60. The dispensing wire 51 is returned to its original position before the next sequence of seeds is created. In another embodiment, in lieu of the arcuate channel and separate nitinol wire, a dispensing wire slidably mated to the door is used to plunge the sequence into the sleeve 62.

Figure 31:
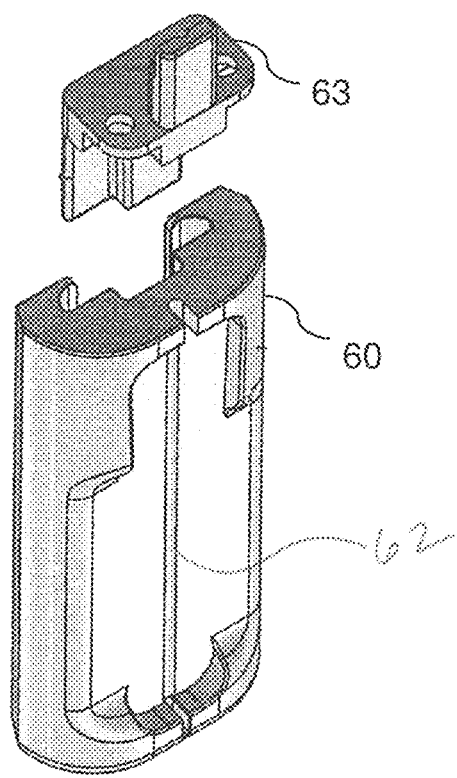
FIG. 31 is an exploded top perspective view of the sleeve holder of the first embodiment.
Figure 32:
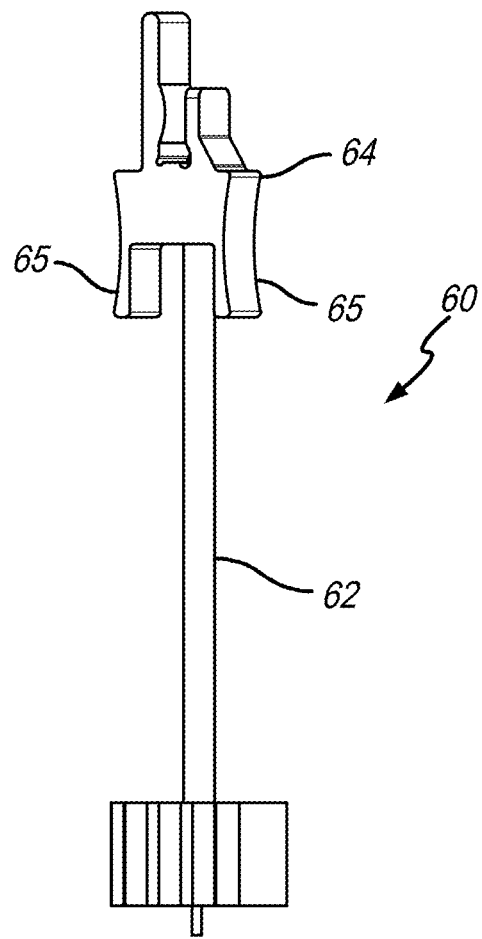
FIG. 32 is a side view of the sleeve holder of the second embodiment.
Figure 33:
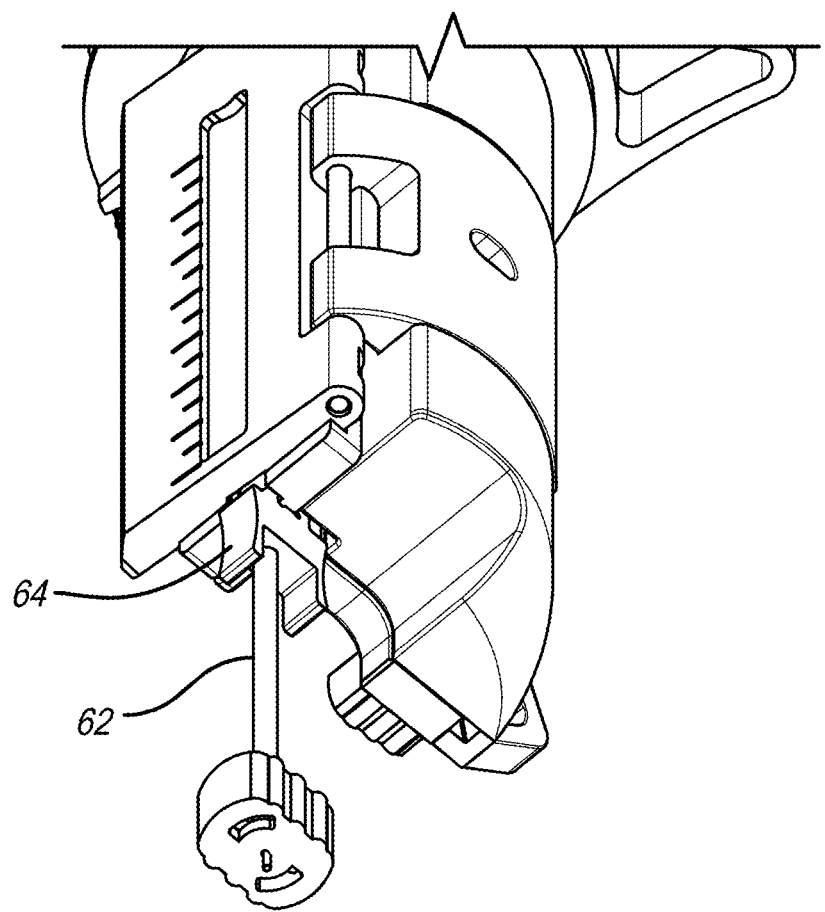
FIG. 33 is a bottom view of the second embodiment of the device with the sleeve holder connected to the inspection assembly.

A sleeve holder 60 is removably attached to the inspection assembly 40 at a mated bracket 63 that is fixed to the inspection assembly 40. In one embodiment shown in FIGS. 1 and 31, the sleeve holder 60 fits in the bracket 63 with a friction fit or snap fit. In a second embodiment shown in FIGS. 32 and 33, the head 64 of the sleeve holder 60 fits in the bracket 63 with a pinch fit. The head 64 has two arms 65 which, when pinched towards each other, release the head 64 from the bracket 63.

Figure 36:
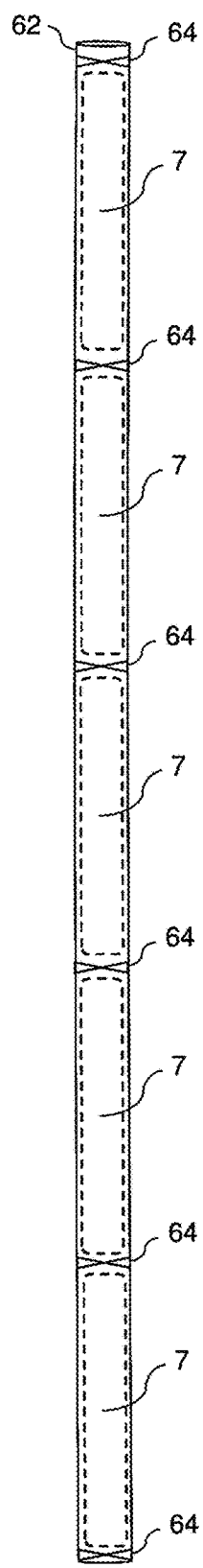
FIG. 36 is a top perspective view of a sleeve formed with pre-spaced compartments.

The sleeve holder 60 initially retains an empty sleeve 62 to receive the sequence from the inspection assembly. Optionally the sleeve 62 may be formed with pre-spaced compartments to hold each pellet in a spaced relationship with the other pellets as they are pushed into place. See FIG. 36. The compartments are separated by resilient barriers 74. Pellets are pushed into the empty sleeve and pushed past each resilient barrier by deforming it. Because the sleeve is made of a resilient material, the barrier then reforms into its original position, blocking the pellet at both ends from moving out of the compartment. Sleeves with pellets held in position with a barrier at each end permits the user to cut off a portion of the filled sleeve at the barrier without having the pellets fall out of the resultant portions of the sleeve. This in turn permits the user to modify the treatment plan quickly by trimming away unwanted pellets, without having to prepare additional filled sleeves or rearrange pellets.

In one embodiment, the resilient barriers 74 are created in the sleeve 62 punching the strand with a sharp needle at about a 45 degree angle relative to the surface of the sleeve. The angled approach is used to make it easier for the needle to penetrate the sleeve without crushing it and to give the proper angle of the burrs to hold the seeds and spacers in the sleeve when they are inserted into the strand by the strand-pusher assembly. As the sleeve is pierced, a burr is created that hangs inside the sleeve 62. This sleeve material that hangs inward acts as a resilient barrier inside the sleeve, which holds the seeds and spacers in place without using any adhesive or heat to seal the sleeve. In another embodiment, the sleeve is pinched or swaged to form the resilient barrier 74. In one embodiment, the sleeve 62 is pierced with a sharp needle to create a series of openings of about 0.20 mm each. These perforations are spaced uniformly on one side of the sleeve at about 1.5 mm and a second of perforations are formed on the opposite side of the sleeve also spaced at about 1.5 mm. See FIG. 20 (not to scale).

The sequence of seeds and spacers within each strand is defined by the needle loading plan for the patient. The sleeves are used to orient, hold, carry, and maintain spacing of the pellets to facilitate introduction into the body during brachytherapy procedures. In a preferred embodiment, a sleeve is made of a material that is compatible with ethylene oxide sterilization, non-reactive, biocompatible, and bioabsorbable within approximately 50 days post-implant. One such sleeve is made of 5/95 PLA/PGA Copolymer, [poly (lactide)/poly(glycolide)], available commercially under the trademark Max-Prene®. Sleeves are supplied non-sterile from the vendor. The sleeves are temperature and moisture sensitive. To prevent degradation of the sleeve in pouches or other containers that are opened for sampling, the remaining sleeve from a sampled container must be stored with a suitable desiccant in a properly labeled, sealed, container.

The sleeves have inside and outside diameters that are compatible with brachytherapy seeds, seed spacers and brachytherapy needles. In one embodiment a sleeve has a nominal inside diameter of 0.034 inch, a nominal outside diameter of 0.038 inch, and a nominal length of 4.7 inches. It may be necessary to cut the sleeve in order to perform required testing or placement.

The device is preferably made of a material that is disposable after a single use. Other embodiment employ re-usable, sterilizable materials having a suitable thickness to shield an operator from radiation emitted by radioactive seeds contained within it. Alternatively, the device may be reusable with some disposable parts.

Figure 35:
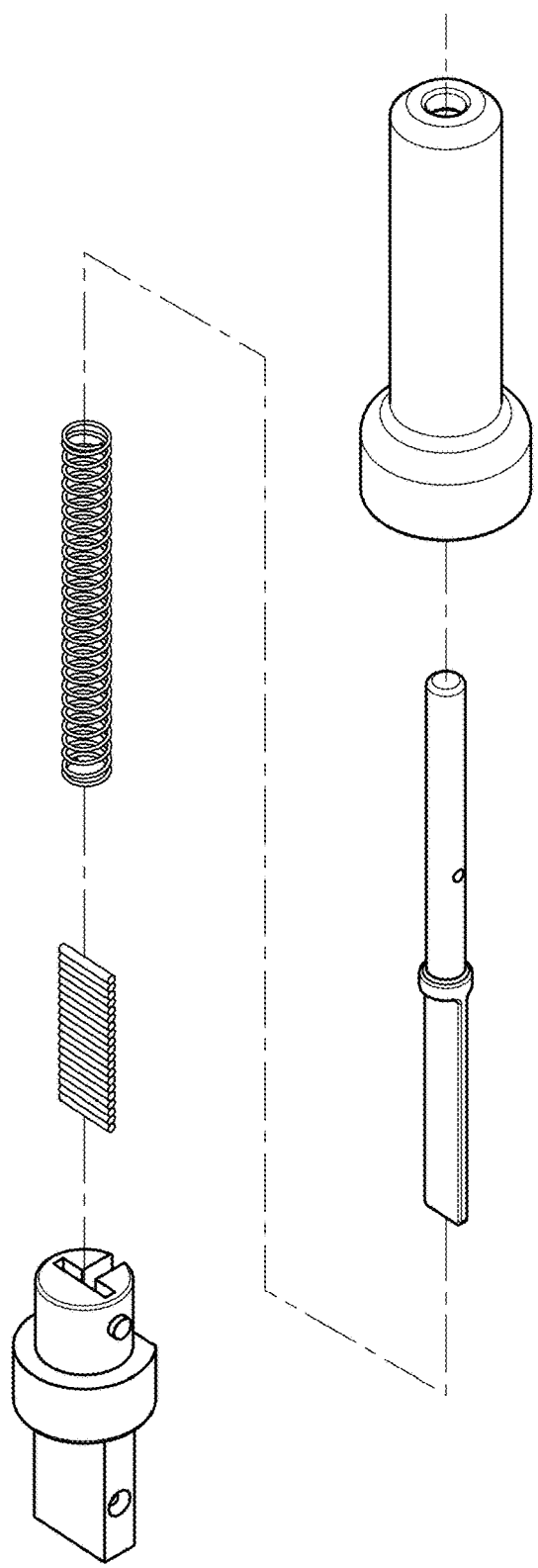
FIG. 35 is an exploded view of a Mick® cartridge of the prior art with a cover of the present invention.

A spring-biased cartridge plunger within the Mick® cartridge biases the pellets forward so that, as one pellet is pushed out, the next pellet is advanced toward the exit hole. Some Mick® cartridges 9 carry radioactive seeds, and some Mick® cartridges 9 carry spacers made of biodegradable material such as wax. The spacers tend to deform and melt together when under a load or passed through high-temperature sterilization. To prevent the spacers in the cartridge from damage during storage and transport, this invention uses a wire insert comprising a plunger pin 92 and a key pin 93 which cooperate to protect the spacers by relieving the pressure on the spacers from the spring bias. See FIG. 35. While the wire insert is in place around the cartridge, the plunger pin 92 retracts the Mick® cartridge plunger from of the stack of spacers. However, without the force on the spacers, they tend to fall out of the exit hole. The key pin 93 blocks the exit hole. The plunger pin 92 and a key pin 93 are removed from the cartridge prior to installing the spacer cartridge into the loader.

While there has been illustrated and described what is at present considered to be the preferred embodiments of the present invention, it will be understood by those skilled in the art that various changes and modifications may be made and equivalents may be substituted for elements thereof without departing from the true scope of the invention. Therefore, it is intended that this invention not be limited to the particular embodiments disclosed, but that the invention includes all embodiments falling within the scope of the appended claims.

The invention claimed is:

1. A device for loading one or more brachytherapy pellets into a sleeve from one or more cartridges, the device comprising:
   a. a selector for selecting a first or second cartridge;
   b. a plunger for pushing a pellet out of the selected cartridge;
   c. a plate having a channel to receive the pellet from the selected cartridge; and
   d. a hinged door attached to the plate, the door having a translucent portion; and
   e. a strand pusher to push the pellet from the channel into the sleeve.

2. The device according to claim 1 wherein:
   a. when the door is closed it encloses the channel and; and
   b. when the door is open it permits the pellet in the channel to be removed from the channel.

3. The device according to claim 1 further comprising forceps slots in the plate.

4. The device according to claim 1 wherein the strand pusher comprises a slidable dispensing wire.

5. The device of claim 1 further comprising a removable sleeve holder which holds the sleeve in communication with the strand pusher as the sleeve receives the pellet as it is pushed from the channel.

6. A device for loading one or more brachytherapy pellets into a sleeve from one or more cartridges, the device comprising:
   a. a turret assembly for selecting from a first or second cartridge;
   b. a plunger assembly for pushing a first pellet out of the first cartridge;
   c. an inspection assembly comprising:
      i. a body having a channel to receive the first pellet from the plunger assembly; and
      ii. a hinged door attached to the body, the door having a translucent portion; and
   d. a strand pusher assembly to push the first pellet from the channel into the sleeve.

7. The device according to claim 6 wherein:
   a. when the door is closed it encloses the channel; and
   b. when the door is open it permits the first pellet in the channel to be moved from the channel.

8. The device according to claim 6 further comprising forceps slots in the body.

9. The device according to claim 6 wherein the strand pusher comprises a slidable dispensing wire.

10. The device of claim 6 further comprising a removable sleeve holder which holds the sleeve in communication with the strand pusher as the sleeve receives the first pellet as it is pushed from the channel.

11. A device for loading one or more brachytherapy pellets into a sleeve from one or more cartridges, the device comprising:
   a. a turret assembly for selecting from a first cartridge and a second cartridge;
   b. a plunger assembly for pushing a first pellet out of the first cartridge and a second pellet out of the second cartridge;
   c. an inspection assembly comprising:
      i. a body having a channel to receive the first pellet and the second pellet from the plunger assembly; and
      ii. a hinged door attached to the body, the door having a translucent portion; and
   d. a strand pusher assembly to push the first pellet and second pellet from the channel into a sleeve connected to the inspection assembly.

12. The device according to claim 11 wherein:
   a. when the door is closed it encloses the channel; and
   b. when the door is open it permits any pellet in the channel to be removed with forceps.

13. The device of claim 11 wherein the turret assembly comprises a selector rod for selecting the first or second cartridge, wherein the selector rod is fixed to a turret head and the turret head is disposed in a rotatable relationship within a turret housing.

14. The device of claim 11 wherein the plunger assembly comprises a plunger to push a plunger pin through a hole in the turret housing through to the selected cartridge to push the first pellet or second pellet out of the selected cartridge.

15. The device of claim 11 wherein the strand pusher assembly comprises:
   a. a slidable dispensing wire in the body;
   b. a tab connected to the dispensing wire to slide the dispensing wire in the channel to push the pellets in the channel into the sleeve.

16. The device of claim 15 wherein the slidable dispensing wire slides in an arcuate channel in the body.

17. The device of claim 15 wherein the slidable dispensing wire slides in a channel in the door.

18. The device of claim 11 further comprising a removable sleeve holder which holds the sleeve in communication with the strand pusher assembly as the sleeve receives the first pellet as it is pushed from the channel.

19. The device of claim 18 wherein the removable sleeve holder has a first end and a second end, and the first end fits in a mated bracket on the strand pusher assembly.

20. The device of claim 11 further comprising one or more stand legs affixed to the turret assembly.

\* \* \* \* \*